United States Patent
Gage (10) Patent No.: US 9,937,057 B2
(45) Date of Patent: Apr. 10, 2018

(54) DELIVERY DEVICE

(71) Applicant: ISTO Technologies, Inc., St. Louis, MO (US)

(72) Inventor: Gary B. Gage, St. Louis, MO (US)

(73) Assignee: ISTO Technologies, Inc., St. Louis, MO (US)

( * ) Notice: Subject to any disclaimer, the term of this patent is extended or adjusted under 35 U.S.C. 154(b) by 171 days.

(21) Appl. No.: 14/035,677

(22) Filed: Sep. 24, 2013

(65) Prior Publication Data

US 2014/0088712 A1    Mar. 27, 2014

Related U.S. Application Data (60) Provisional application No. 61/704,961, filed on Sep. 24, 2012.

(51) Int. Cl.

| A61F 2/44 | (2006.01) |
| A61F 2/46 | (2006.01) |
| A61B 17/88 | (2006.01) |

(52) U.S. Cl.
CPC ........ *A61F 2/4601* (2013.01); *A61B 17/8816* (2013.01); *A61B 17/8825* (2013.01); *A61F 2/4455* (2013.01)

(58) Field of Classification Search
CPC ......... A61B 17/3421; A61B 17/8802–17/8847
See application file for complete search history.

(56) References Cited

U.S. PATENT DOCUMENTS

| 3,765,497 A | 10/1973 | Thordarson | |
| 4,277,184 A * | 7/1981 | Solomon | A61B 17/8822 366/139 |
| 4,768,521 A | 9/1988 | Schiffman et al. | |
| 5,270,685 A | 12/1993 | Hagen et al. | |
| 5,375,596 A * | 12/1994 | Twiss | A61B 5/06 128/903 |
| 5,398,483 A * | 3/1995 | Smith et al. | 53/474 |
| 6,241,734 B1 * | 6/2001 | Scribner | A61B 17/8816 606/93 |
| 6,626,902 B1 * | 9/2003 | Kucharczyk | A61B 5/14503 606/34 |
| 8,308,731 B2 * | 11/2012 | Valaie | 606/92 |
| 2002/0010431 A1 * | 1/2002 | Dixon et al. | 604/221 |
| 2003/0028196 A1 * | 2/2003 | Bonutti | A61B 17/025 606/87 |
| 2004/0245163 A1 * | 12/2004 | Lim | B01D 61/18 210/323.1 |
| 2006/0079905 A1 * | 4/2006 | Beyar | A61B 17/7095 606/76 |
| 2006/0211912 A1 | 9/2006 | Dlugos et al. | |
| 2007/0173946 A1 * | 7/2007 | Bonutti | A61B 17/025 623/20.14 |

(Continued)

OTHER PUBLICATIONS

International Search Report and Written Opinion regarding PCT/US2012/037548 dated Sep. 7, 2012, 7 pages.

*Primary Examiner* — Jan Christopher Merene
*Assistant Examiner* — Steven Controneo
(74) *Attorney, Agent, or Firm* — Polsinelli PC (57) ABSTRACT

The present disclosure provides a delivery device for delivering a tissue repair composition in paste form, such as a bone graft extender and substitute in paste form, for use in surgical procedures including minimally invasive spine (fusion) surgery, open spine surgery and other orthopedic procedures.

36 Claims, 8 Drawing Sheets

(56) References Cited

U.S. PATENT DOCUMENTS

2009/0093726 A1\* 4/2009 Takayama .............. A61B 8/12
                                                                    600/466
2011/0009812 A1    1/2011 Brown
2012/0323299 A1\* 12/2012 Greenberg ............. A61F 2/07
                                                                     623/1.11

\* cited by examiner

DELIVERY DEVICE

CROSS REFERENCE TO A RELATED APPLICATION

This application claims priority from U.S. Provisional Application Ser. No. 61/704,961 filed on Sep. 24, 2012, the disclosure of which is hereby incorporated by reference in its entirety.

TECHNICAL FIELD

This invention relates to delivery devices for bone graft extender compositions, and related methods.

BACKGROUND

Many surgical procedures involve the delivery of compounds or compositions to promote and support tissue repair. Orthopedic surgical procedures, such as spinal fusion for example, commonly involve the delivery of bone grafts or compositions containing bone grafts to a bone site in need of repair. In some cases, minimally invasive surgical procedures (MIS) can be advantageously deployed, wherein the bone graft compound or composition can be delivered and applied to tissue with a minimum of using a reduced surgical access site.

Bone graft compounds and compositions are often provided in a paste form in which autogenous or allogaft bone granules or chips are used. Particularly during MIS procedures, but also during open surgeries, delivery of such paste compositions can be difficult because of limited viewing and limited access to the tissue site in need of repair. A need exists for improved delivery systems and methods for delivering tissue repair compositions having a paste form, to a tissue site in need of repair, especially for bone repair.

SUMMARY

In one aspect, the present disclosure provides a delivery system for delivering a tissue repair paste composition to a tissue site in need of repair, the system comprising: an elongate housing defining a chamber for receiving the paste composition and having a proximal end and a distal end having an external surface; a plunger slidably disposed within the chamber; a flexible tube defining a lumen and having a proximal end defining a fitting having an internal surface configured to reversibly engage with the external surface of the housing distal end; a metal wire coupled to the flexible tube; a flexible tamping element comprising a flexible rod configured to be slidably disposed within the lumen of the flexible tube; a substantially rigid tube defining a lumen and having a proximal end defining a fitting having an internal surface configured to reversibly engage with the external surface of the housing distal end; and a substantially rigid tamping element comprising a substantially rigid rod configured to be slidably disposed within the lumen of the substantially rigid tube. The delivery system can further comprise a cap having a peripheral wall defining a fastening element configured to reversibly engage the external surface of the chamber distal end, thereby sealing the distal end of the chamber. The cap can further comprise a sealed female Luer Lok or Luer Slip fitting. In the delivery system, the flexible tube can have a length greater than the length of the substantially rigid tube. The flexible tamping element and the substantially rigid tamping element can each have a proximal end defining a flange. The flexible tamping element and the substantially rigid tamping element can each have a distal end, the distal end of the flexible tamping element configured for insertion into the lumen of the flexible tube, and the distal end of the substantially rigid tamping element configured for insertion into the lumen of the substantially rigid tube. The flexible tube can have a distal end and comprises a peripheral wall, wherein the delivery system further comprises the metal wire, such as a stainless steel wire, coupled to or embedded in the wall, and extending from the proximal end to the distal end of the flexible tube. The metal wire can terminate at the distal end of the flexible tube and be capable of transmitting an imaging signal, such as a fluoroscopy signal from the distal end of the flexible tube.

The fitting at the first end of the flexible tube and the fitting at the first end of the substantially rigid tube can be each configured to provide fluid communication between the housing chamber and the central openings of the flexible tube and the substantially rigid tube. The flexible tamping element may comprise a material having shape memory. The flexible tamping element can comprise polycarbonate. The flexible tube can comprise polyurethane, and may further comprise silicone impregnated in the polyurethane. The flexible tube may comprise a peripheral wall having an inner surface, the inner surface having a plurality of depressions randomly distributed thereon, or the inner surface may have a coating of a non-stick polymer such as polytetrafluoroethylene (PTFE). The chamber housing can have for example a volume of at least about 5 cubic centimeters ($c^3$). The chamber housing may comprise a transparent plastic.

In another aspect, the present disclosure provides a method for delivering a tissue repair paste to a tissue site, the method comprising: (a) loading the tissue repair paste into the housing chamber of the delivery system according to claim 1; (b) selecting a tamping pair from a first tamping pair consisting of the flexible tube and the flexible tamping element, and a second tamping pair consisting of the substantially rigid tube and the substantially rigid tamping element; (c) coupling the proximal end of the selected tube to the distal end of the housing; (d) depressing the plunger within the chamber thereby forcing the tissue repair paste through the distal end of the chamber and into the lumen of the selected tube; decoupling the housing from the selected tube; (e) inserting the distal end of the selected tamping element into the lumen of the selected tube at proximal end of the selected tube; and (f) impelling the tamping element through the lumen of the selected tube, thereby forcing the tissue repair paste through the lumen of the selected tube to deliver the tissue repair paste to the tissue site. In any of the methods, the tissue site can be a bone site, and the tissue repair paste can be a bone graft paste composition.

Initially in the method, the tamping pair selected in step (b) can be the flexible tamping pair, and the method can further comprise: (g) decoupling the flexible tube from the housing distal end; (h) coupling the proximal end of the substantially rigid tube to the housing distal end; (i) depressing the plunger within the chamber thereby forcing the tissue repair paste through the distal end of the chamber and into the lumen of the substantially rigid tube; decoupling the housing from the substantially rigid tube; (j) inserting the distal end of the substantially rigid tamping element into the lumen of the substantially rigid tube at the proximal end of the substantially rigid tube; and (k) impelling the substantially rigid tamping element through the lumen of the substantially rigid tube, thereby forcing the tissue repair paste through the lumen of the substantially rigid tube to further deliver the tissue repair paste to the tissue site.

Alternatively, initially in the method, the tamping pair selected in step (b) is the substantially rigid tamping pair, and the method further comprises: (g) decoupling the substantially rigid tube from the housing distal end; (h) coupling the proximal end of the flexible tube to the housing distal end; (i) depressing the plunger within the chamber thereby forcing the tissue repair paste through the distal end of the chamber and into the lumen of the flexible tube; decoupling the housing from the flexible tube; (j) inserting the distal end of the flexible tamping element into the lumen of the flexible tube at the proximal end of the flexible tube; and (k) impelling the flexible tamping element through the lumen of the flexible tube, thereby forcing the tissue repair paste through the lumen of the flexible tube to further deliver the tissue repair paste to the tissue site. When the tamping pair selected in step (b) is the flexible tamping pair, the method can further comprise flexing the flexible tube to form a bend in the tube, thereby to improve a surgical approach to the tissue site relative to a surgical approach obtained with a straight tamping pair. The method can further comprise flexing the flexible tamping element to form a corresponding bend in the flexible tamping element. In the methods, the tissue site can be a spinal site being approached using a TLIF (transforaminal interbody fusion) approach or a PLIF (posterolateral interbody fusion) approach, the tissue repair paste comprises a bone graft paste composition, and the flexible tube can be bent to deliver the bone graft paste composition to a contra-lateral space of the disc.

In another aspect, the present disclosure provides a kit for delivering a tissue repair paste to a tissue site, the kit comprising: a tray comprising a sterilizable material; and disposed in the tray, a plurality of components of a delivery system for delivering the tissue repair paste to the tissue site, the components comprising: an elongate housing defining a chamber for receiving the paste composition and having a proximal end and a distal end having an external surface; a plunger slidably disposed within the chamber; a flexible tube defining a lumen and having a proximal end defining a fitting having an internal surface configured to reversibly engage with the external surface of the housing distal end; a metal wire coupled to the flexible tube; a flexible tamping element comprising a flexible rod configured to be slidably disposed within the lumen of the flexible tube; a substantially rigid tube defining a lumen and having a proximal end defining a fitting having an internal surface configured to reversibly engage with the external surface of the housing distal end; and a substantially rigid tamping element comprising a substantially rigid rod configured to be slidably disposed within the lumen of the substantially rigid tube. The components of the delivery system included in the kit can include a cap having a peripheral wall defining a fastening element configured to reversibly engage the external surface of the chamber distal end, thereby sealing the distal end of the chamber. In the kit, any of the components of the delivery system can be as described herein above. The kit can further comprise an amount of the tissue repair paste, such as a bone graft repair paste, in a separate container, or may further comprise amounts of at least two reagents for preparing the tissue repair paste. The kit may further comprise a sealed cover sealing the tray. The kit may further comprise a sealed pouch enclosing the tray and delivery system components disposed therein.

DETAILED DESCRIPTION

The delivery system described herein comprises a device configured for the application of tissue repair compositions to the tissue in need of repair, wherein the tissue repair composition is a paste. The delivery system is useful, for example, in delivering a bone graft paste composition to bone tissue during orthopedic surgeries including minimally-invasive surgeries (MIS), and to bone voids, and hard-to-reach areas of bone. In non-limiting example, the delivery system can be used to deliver InQu® Bone Graft Extender & Substitute (ISTO Technologies, Inc.) to bone in need of repair. The delivery system provides improved control of the delivery and/or application of a bone graft paste composition to a bone site in need of repair. It is contemplated that the delivery system can be used for example in both minimally invasive spine (fusion) surgery, and open spine surgery, as well as other orthopedic procedures.

Figure 1:
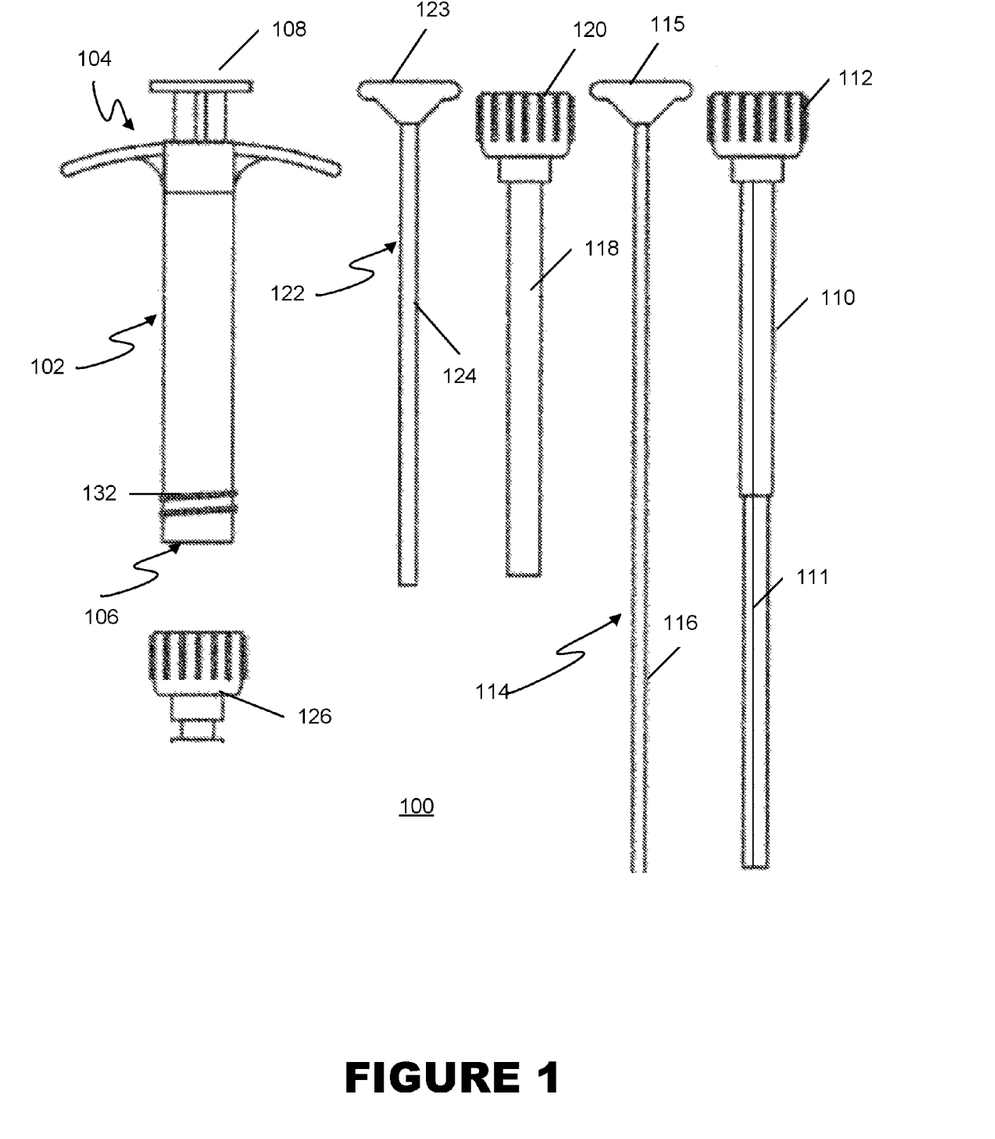
FIG. 1 is a schematic diagram of components of a delivery system for delivering a tissue repair paste composition to a tissue site in need of repair.

As shown in FIG. 1, a delivery system 100 includes an elongate housing 102 defining a chamber for receiving the paste composition and having a proximal end 104 and a distal end 106 having an external surface; a plunger 108 slidably disposed within the chamber; a flexible tube 110 defining a lumen and having a proximal end defining a fitting 112 having an internal surface configured to reversibly engage with the external surface of the housing distal end; a metal wire coupled to the flexible tube 111; a flexible tamping element 114 comprising a flexible rod 116 configured to be slidably disposed within the lumen of the flexible tube; a substantially rigid tube 118 defining a lumen and having a proximal end defining a fitting 120 having an internal surface configured to reversibly engage with the external surface of the housing distal end; and a substantially rigid tamping element 122 comprising a substantially rigid rod 124 configured to be slidably disposed within the lumen of the substantially rigid tube. The delivery system can further comprise a cap 126 having a peripheral wall defining a fastening element configured to reversibly engage the external surface of the chamber distal end, thereby sealing the distal end of the chamber. Flexible tube 110 and flexible tamping element 114 form a flexible tamping pair, and substantially rigid tube 118 substantially rigid tamping element 122 form a substantially rigid tamping pair.

Any and all of the system components, including a tray as described herein below, can be manufactured according to plastic manufacturing methods as well known in the art, such as but not limited to extrusion, various moulding and forming processes and most currently, 3-D printing. Unless otherwise indicated, all components can comprise any plastic which can suitably withstand routine sterilizing procedures such as an ethylene oxide sterilization cycle. For example, any of the components can be manufactured from polyurethane. Certain components can be made using a transparent plastic, such as housing 102 and either or both of tubes 110 and 118. Though not required, preferably all components are latex-free. The delivery system components can be manufactured such that each component is substantially symmetrical, such that both right-handed and left-handed users can use the delivery system with the same ease.

It will be understood that the dimensions of housing 102, flexible and substantially rigid tubes (110 and 118), and flexible and substantially rigid tamping elements (114 and 122) can vary within ranges of length and width normally used for manual instruments used in surgical procedures, provided that the flexible components have dimensions consistent with flexibility and shape memory as described herein. In one delivery system, the housing chamber can accommodate a volume of at least about 5 cubic centimeters of a tissue repair paste composition. Housing 102 preferably has a full-bore opening at the proximal end to facilitate loading of prepared tissue repair paste, such as a bone graft paste.

The dimensions of each component of a tamping pair are such that the tamping element of the pair slidably engages with the lumen of the corresponding tube. In non-limiting example, a delivery system can include a flexible tube 110 having an outer diameter of about 6 mm, and a length of about 180 mm. The rod 116 of corresponding flexible tamping element 114 has an outer diameter which permits easy insertion into the lumen of the flexible tube 110, and a length exceeding the length of flexible tube 110, for example more than 180 mm, to allow the distal end of flexible tamping element 114 to reach the distal end of flexible tube 110 when inserted into the lumen. Substantially rigid tube 118 can have for example an outer diameter of about 8 mm, and a length of about 150 mm. The rod 124 of corresponding substantially rigid tamping element 122 has an outer diameter which permits easy insertion into the lumen of substantially rigid tube 118, and a length exceeding the length of substantially rigid tube 118, for example more than 150 mm, to allow the distal end of rod 124 to reach the distal end of substantially rigid tube 118 when inserted into the lumen.

Figure 2:
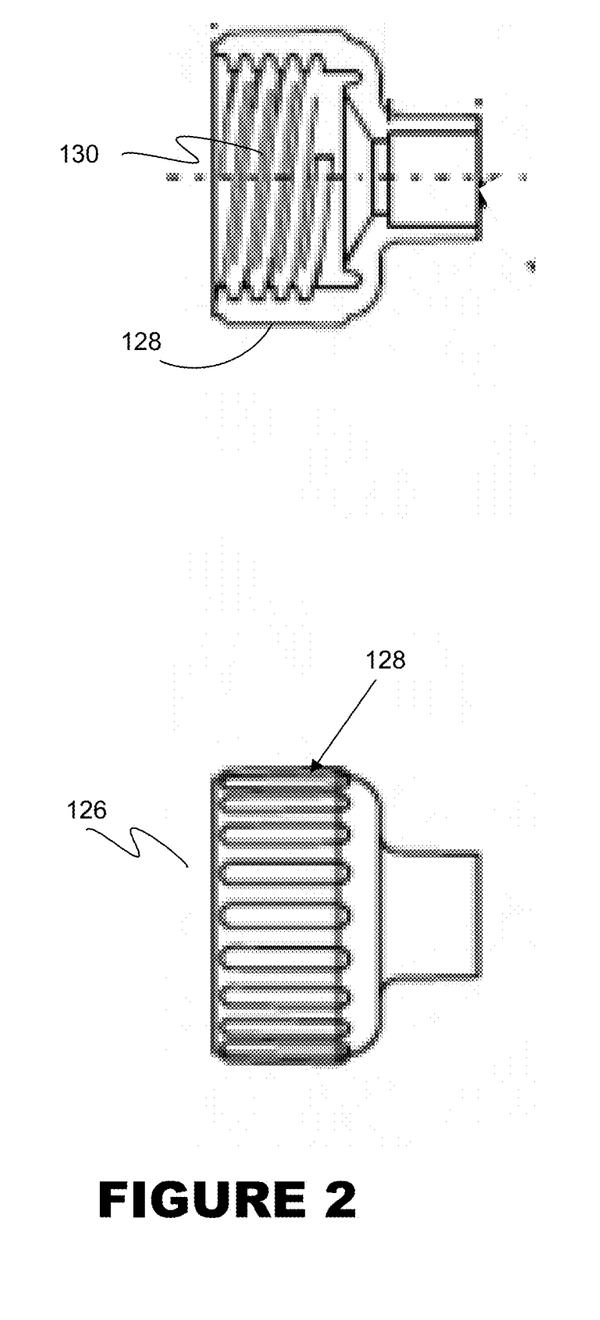
FIG. 2 is two side views of a cap used in the delivery system, including a transparent view of the cap peripheral wall.
Figure 3:
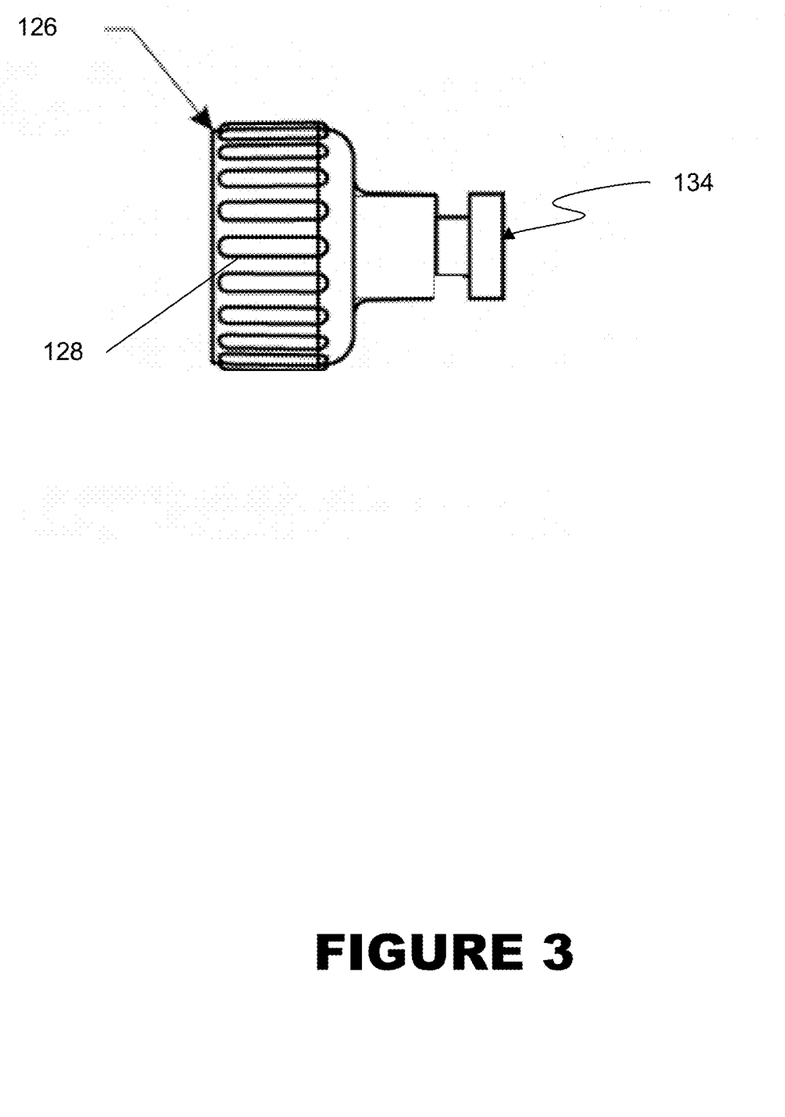
FIG. 3 is a side view of the cap shown in FIG. 2 coupled to a female Luer Lok fitting.

FIGS. 2 and 3 provide views of cap 126. FIG. 2 provides a side view of cap 126, showing cap peripheral wall 128. The transparent view of cap 126 shows internal surface of peripheral wall 128 defining a female fitting having a plurality of spiral grooves 130 configured to reversibly engage corresponding spiral threads 132 on a male fitting defined by the external surface of the chamber distal end 106 (see FIG. 1). Thus cap 126 can be screwed on and secured to chamber distal end 106 to prevent drying of the tissue repair composition during a procedure thereby sealing the distal end of the chamber, for example after the tissue repair composition has been loaded into the chamber of housing 102, but before application if the composition to the tissue. FIG. 3 shows a side view of cap 126 coupled to a sealed or sealable female Luer fitting 134.

Figure 4:
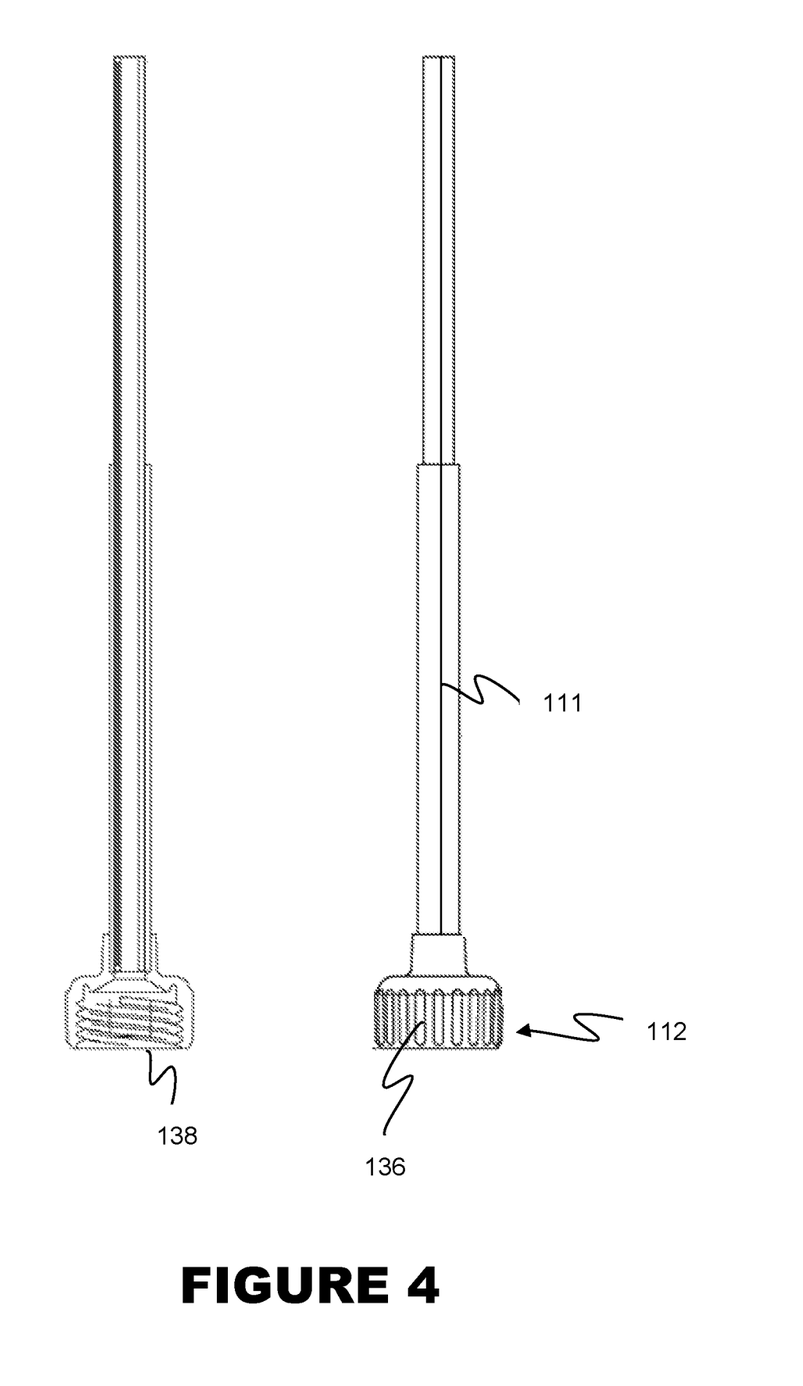
FIG. 4 is a side view of a flexible tube in the delivery system.
Figure 6:
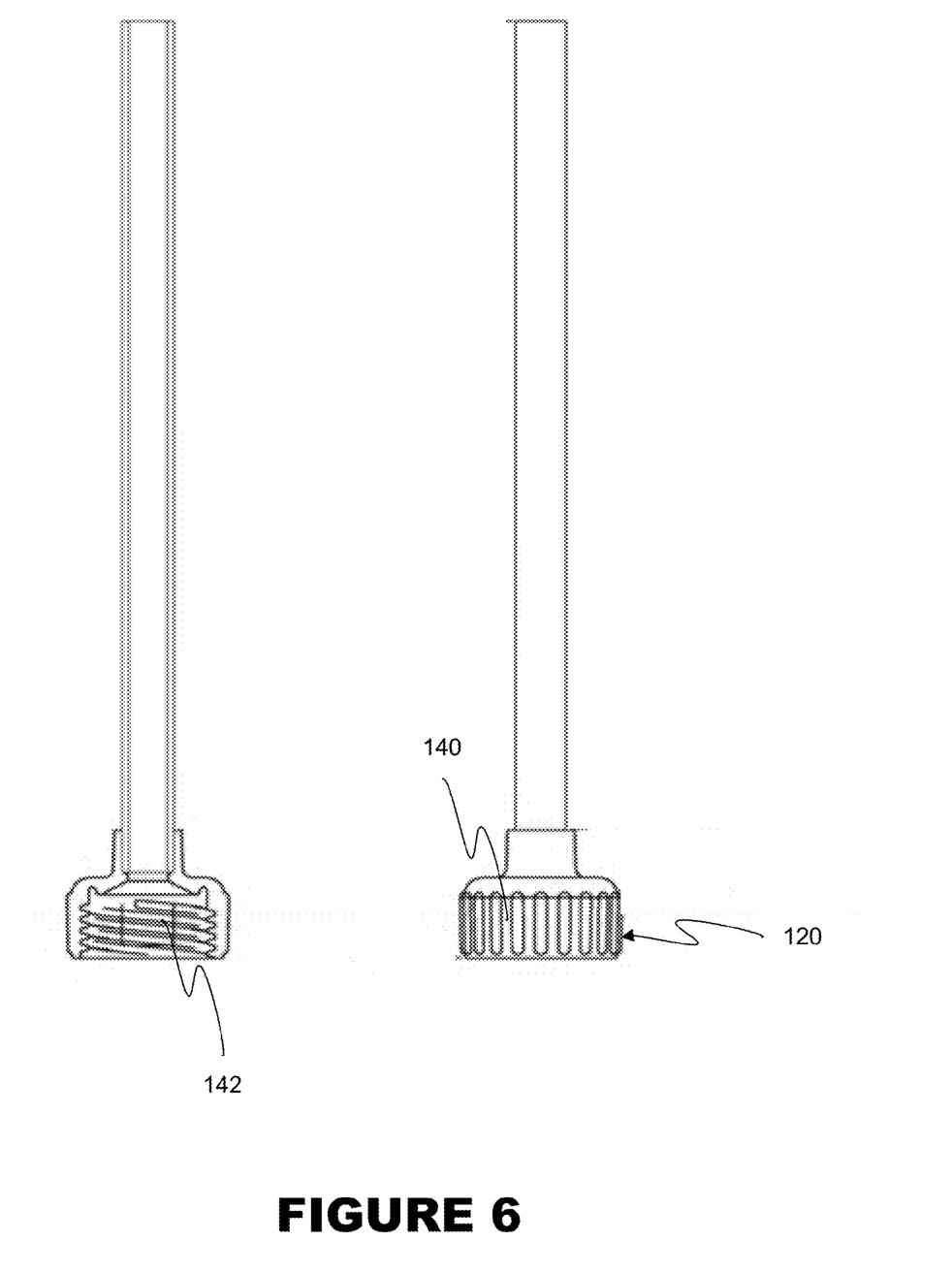
FIG. 6 is a side view of a substantially rigid tube in the delivery system.

As shown in FIGS. 4 and 6, fittings 112 and 120 on tubes 110 and 118 can have essentially the same configuration as cap 126 in terms of the fastening element for fastening to chamber distal end 106. For example, as shown in FIG. 4, fitting 112 defines a peripheral wall 136 defining a female fitting having a plurality of spiral grooves 138 configured to reversibly engage corresponding spiral threads 132 defined by the external surface of the chamber distal end 106 as shown in FIG. 1. Similarly, as shown in FIG. 6, fitting 120 defines a peripheral wall 140 defining a female fitting having a plurality of spiral grooves 142 configured to reversibly engage corresponding spiral threads 132 defined by the external surface of the housing distal end 106 as shown in FIG. 1 It should be understood however that in the any of fitting 112, fitting 120, and cap 126, the peripheral wall can alternatively be configured in various ways as known in the art to provide alternative means for defining or providing a fastening element configured to reversibly engage the external surface of the chamber distal end. Corresponding adaptions of housing distal end 106 can be made. For example, the peripheral wall of any of fitting 112, fitting 120, and cap 126 can be configured so as to define other features such as ribs, detents, pins or catches which can reversibly engage corresponding fastening elements made on the external surface of housing distal end 106.

Cap 126 and tubes 110 and 118 are thus readily detachable from housing 102 and are interchangeable with one another. It is contemplated for example that during a single procedure, any one or all of cap 126, tube 110 and tube 118 may be used. For example, in surgical procedures for repairing the spine, the delivery system can be prepared and loaded with a bone paste composition before or at the start of the procedure, and distal end 106 sealed with cap 126. When the surgeon needs to deliver the bone paste composition to a bone site, cap 126 is removed, flexible tube 110 is secured to distal end 106, and the flexible tamping pair used to initially deliver the bone paste to intervertbral (disc) space (s), as described further below. Subsequently, flexible tube 110 can be removed and substantially rigid tube 118 secured to distal end 106, and the substantially rigid tamping pair used to deliver a higher volume of bone paste to postero-lateral space(s) ("360 surgeries".)

As used herein with respect to flexible tube 110 and flexible tamping element 114, the term "flexible" refers to the ability of tube 110 and tamping element 114 to be bent at an angle of as much as 90 degrees or even further, and not break. Further, the materials used for making flexible tube 110 and flexible tamping element 114 have shape memory in that once a bending force is removed, each component slowly recovers its initial, straight shape. For flexible tube 110, this is achieved by using a malleable although yet semi-rigid plastic such as polyurethane, and coupling thereto or embedding in the plastic a wire such as an annealed stainless steel wire. Preferably, a transparent plastic is used to allow visualization of the tissue repair paste during use. Preferably, a plastic which has some shape memory is used, so that flexible tube 110 can recover an initial straight shape after being bent during use.

It will be appreciated that the malleability and deformability of flexible tube 110, either alone or together with flexible tamping element 114 inserted therein, allows the surgeon to better direct and control the flow of a tissue paste repair paste composition to a specific tissue site. For example, tube 110 can be bent as needed up to at least 90 degrees, to better achieve a variety of surgical site approaches for delivering a bone graft paste to the disc space into the desired disc space location. This is particularly useful for example in the rear-lateral position used in the TLIF (transforaminal interbody fusion) or in the PLIF (posterolateral interbody fusion) approaches used in many MIS surgeries. Flexible tube 110 can be manually bent up to at least 90 degrees to ensure that bone graft paste is delivered to the contra-lateral space of the disc. The same is true for surgical approaches used in PLIF (posterolateral interbody fusion) approaches.

Flexible tube 110 includes a metal wire 111 running at least the length of the tube from distal end to the proximal end. The wire is for example a stainless steel wire, which can be annealed stainless steel. The wire can be for example embedded in the body of the tube, or otherwise fastened, for example adhered to the tube. In combination with the plastic used for flexible tube 110, the wire provides flexibility, strength and shape memory sufficient to allow bending of flexible tube in use, while at the same time, recovery of the initial straight shape as needed. For example, while in use at any time, flexible tube can be bent in situ (i.e., at or in the tissue site) to provide improved access and delivery of the paste composition to the tissue site. Flexible tube 110 can be bent with or without flexible tamping element 114 inserted therein. Once a sufficient amount of paste is delivered to the tissue site, flexible tube can be withdrawn and manually straightened, for example to allow for an improved back-fill of the site entry as flexible tube 110 is being withdrawn. Alternatively, flexible tube can be withdrawn and left in a bent position, with or without flexible tamping element inserted therein 114, to better act as a scarping tool to remove excess paste composition from the entry to the tissue site.

The wire terminates at the distal end of the tube. This allows the wire to be used for visualization of tissue proximal to the distal end of the tube, and also of the flow of the tissue repair paste, using fluoroscopy. For example, the distal end of flexible tube 110, when in use, can be positioned in contact with or adjacent to a bone site, and the flow of bone graft paste into the bone site can be visualized during delivery of the bone graft paste to the bone site.

It will be appreciated that the lumen of flexible tube 110 and the lumen of substantially rigid tube 118 are defined by a peripheral wall of the tube, and that the peripheral wall has an internal surface. Preferably, the internal surface of each tube is sufficiently lubricious to easily allow passage of the tissue repair paste through the tube, even in the case of flexible tube 110 when bent to a curve. This can be accomplished in multiple ways, for example by manufacturing the tubes with an "orange-peel" like internal surface, i.e., a plurality depressions randomly distributed thereon. This is preferably accomplished when the wire is coupled to flexible tube 110 by embedding in the wall of the tube during a slow extrusion of the plastic (polyurethane). While a conductor such as a wire can later be inserted into a lumen formed in the wall of the tube during extrusion, a sufficient "orange peel effect" is less easily achieved. A slow extrusion process produces an optimal "orange peel effect".

Alternatively the internal surface of each tube is made sufficiently lubricious by coextruding the plastic with a coating of a polytetrafluoroethylene (PTFE) on the inner surface, or by impregnating the plastic with silicone.

Extrusion of a tube to form a lumen within the peripheral wall of the tube in the wall and subsequent insertion of a wire as the conductor into the lumen means that the wire can be constrained only at one or the other end (either the distal end or the proximal end) of the tube, and left unconstrained in the rest of the lumen. This makes bending of the flexible tube in virtually any direction easier and particularly improves the capability of the flexible tube to bend about a perpendicular plane.

Figure 5:
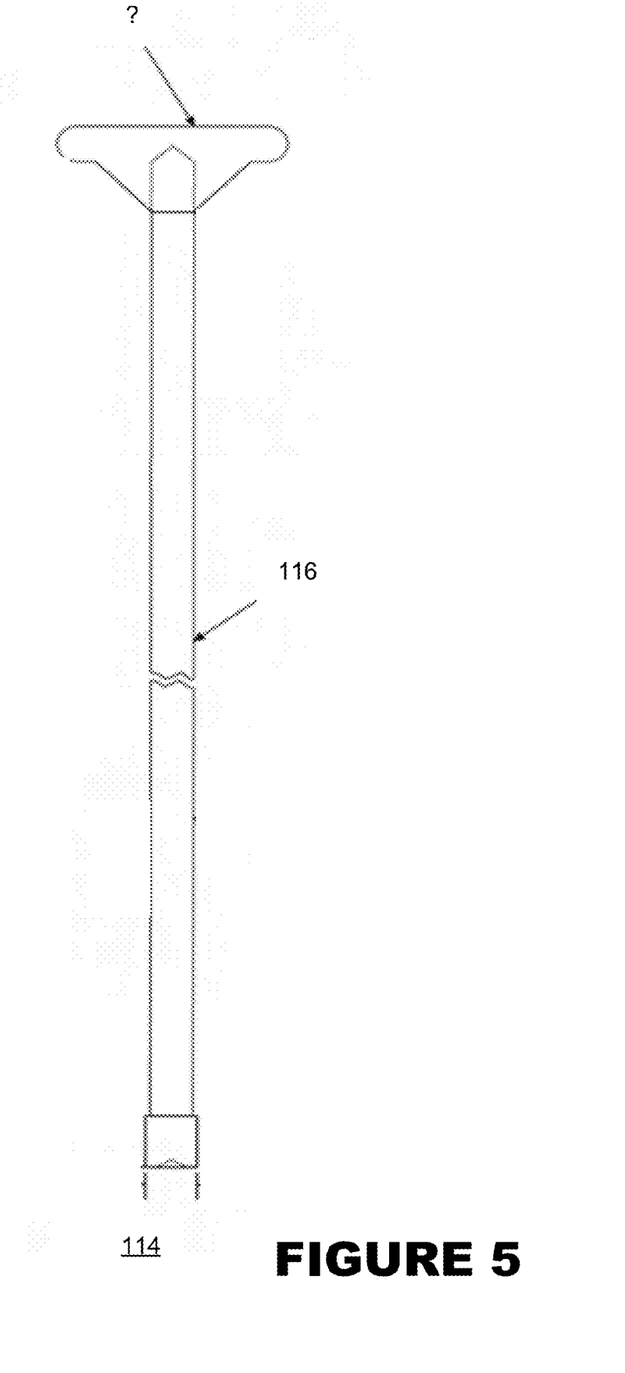
FIG. 5 is a side view of a flexible tamping element in the delivery system.
Figure 7:
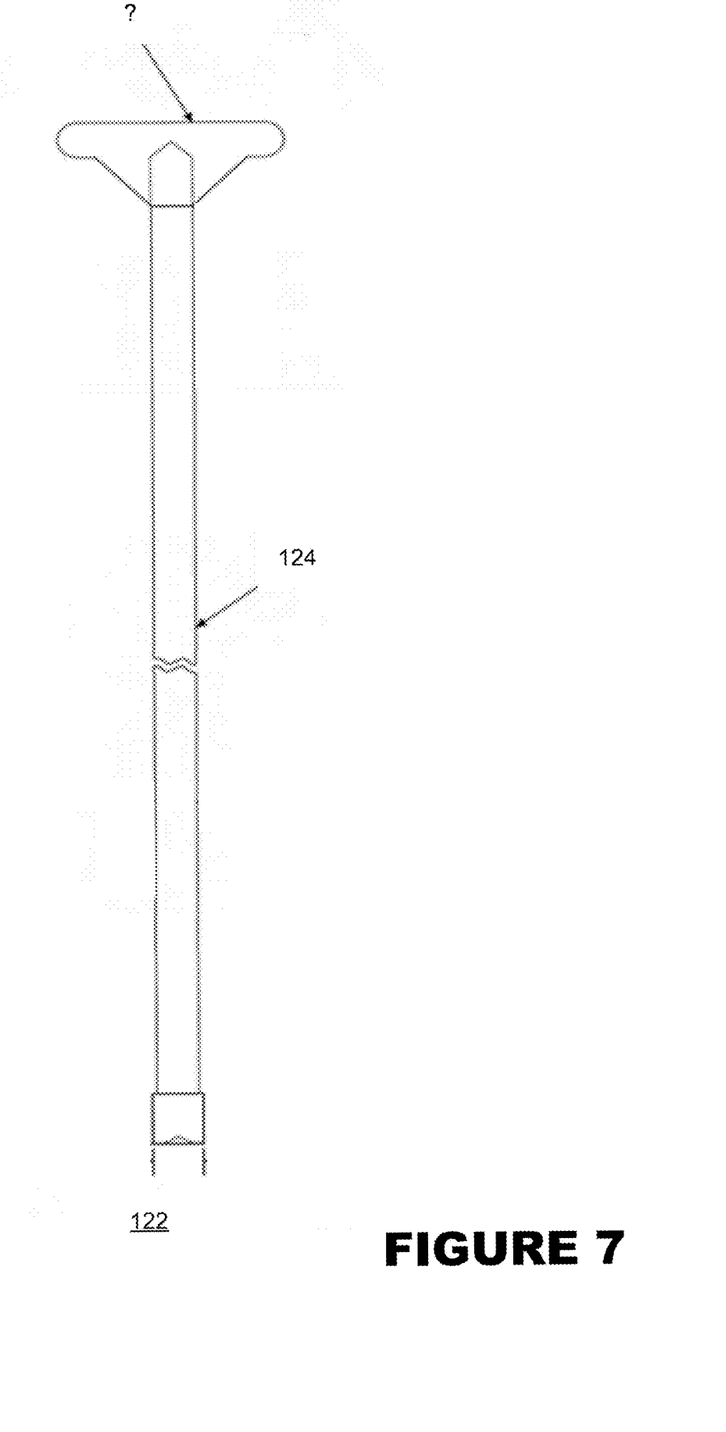
FIG. 7 is a side view of a substantially rigid tamping element in the delivery system.

Flexible tamping element 114 comprises a malleable plastic such as but not limited to polycarbonate. Preferably, a plastic which has some shape memory is used, so that flexible tamping element 114 can also retain a bent shape obtained upon manual bending of tamping element 114 during use, as needed to reach an otherwise difficult to access tissue site. Flexible tamping element 114 can for example be inserted in flexible tube 110 and manually bent together with flexible tube 110 as described above. Either or both of flexible tamping element 114 and substantially rigid tamping element 122 can each have a proximal end defining a flange. As shown in FIGS. 1, 5 and 7 for example, flexible tamping element 114 has a flange 115, and substantially rigid tamping element 122 has a flange 123. Such flanges facilitate manual handling and control of the tamping elements in use.

Both or either of tamping elements 114 and 122 can be radiofrequency (RF) tipped to form a larger outer diameter at the tip, i.e., distal end, relative to the proximal end of each tamping element. This allows for minimal drag as the tamping element advances through the corresponding tube.

Figure 8:
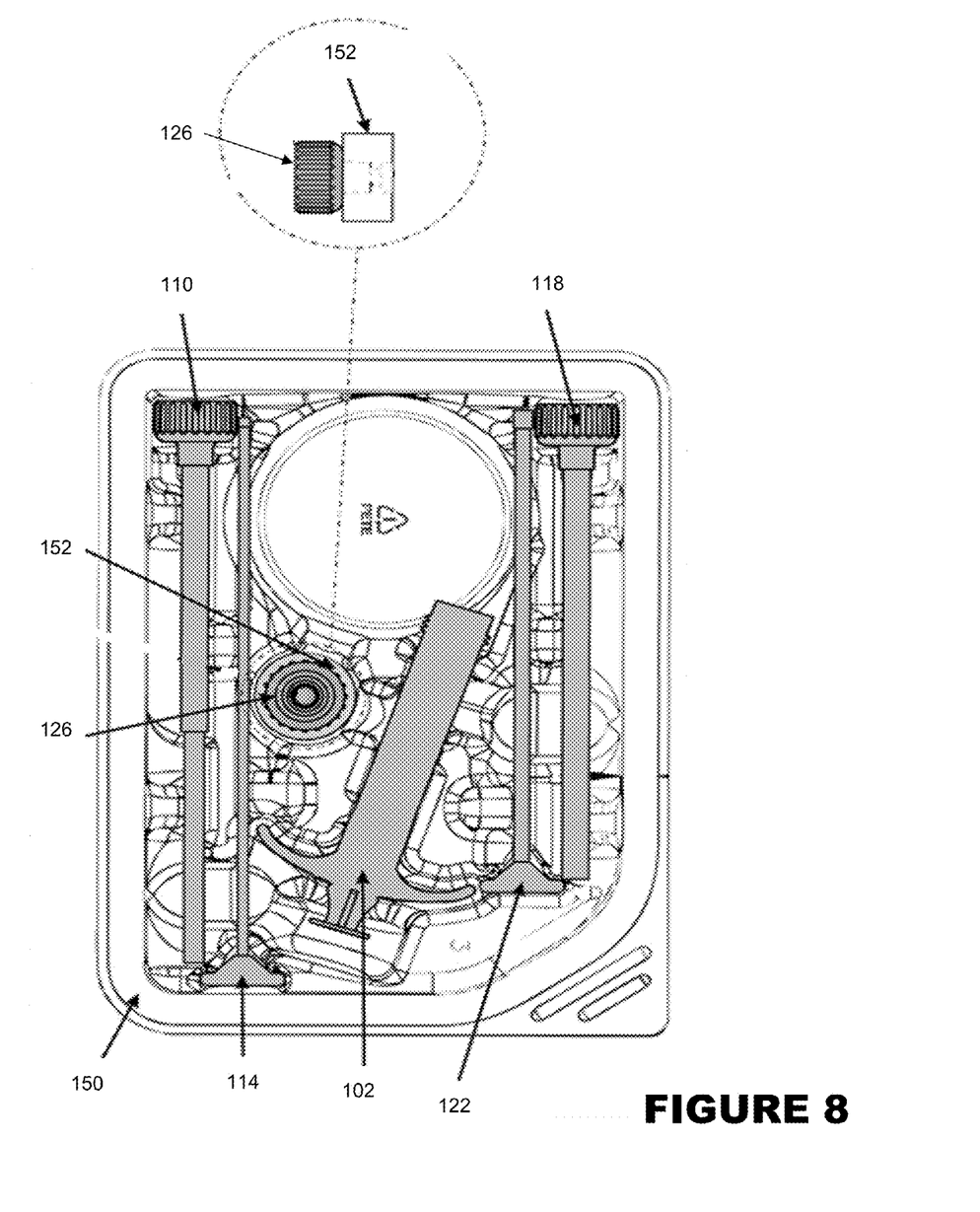
FIG. 8 is a plan view of a kit comprising the delivery system components fitted in a tray.

The present disclosure also contemplates a kit for delivering a tissue repair paste to a tissue site. The kit can comprise for example any one or all of the components of the delivery system as described herein, disposed in a tray comprising a sterilizable material, such as a plastic, for example polyurethane. As shown in FIG. 8, a kit comprises a thermoformed tray 150, and all components of delivery system 100 disposed in tray 150. Tray 150 may be formed for example with a plurality of well each variously shaped to receive and stabilize each component in tray 150. A kit may further include a foam ring 152 configured to substantially conform to the narrowest portion of cap 126 and fit into a corresponding well for cap 126 and thereby stabilize cap 126. Tray 150 can be sealed with any suitably strong yet breathable synthetic material, such as flashspun high-density polyethylene fibers, available as Tyvek® from DuPont. Tray 150 can further be enclosed in a pouch (not shown) made of a suitably strong packaging material, and preferably one which provides a sterile barrier to outside contaminants and moisture prior to introduction of tray 150 into a sterile surgical field, while at the same time while at the same time allowing permeation of sterilizers to facilitate device sterilization. For example, the pouch can be made of Tyvek® and/or poly low-density polyethylene (LDPE). The combination of tray 150 and pouch can be further packaged in a moisture resistant outer container such as a carton.

The kit may further comprise an amount of the tissue repair paste, such as an amount of a bone graft paste, in a separate container, or two or more components for preparing a bone graft paste in multiple, separate containers. The kit can further comprise a sealed cover on the tray, and/or a sealed pouch enclosing the tray and delivery system components disposed therein.

To use the delivery system, the user opens outer, non-sterile packaging and inner, sterile, packaging. The tissue repair paste composition is prepared according to manufacturer's directions. For example, InQu® Bone Graft Extender & Substitute can be prepared as directed from InQu® Paste Mix PLUS per the manufacturer's Directions for Use. Care should be taken to prepare any solid particle or granules to the smallest possible size to help avoid clogging the tubes. For example, when combining InQu® Paste Mix PLUS with autograft for use with the PLUS Delivery System, care should be taken to prepare autograft shavings down to the smallest size possible, i.e., less than about 2 mm in size, for example by using sing a high-speed burr. The prepared tissue repair paste composition is loaded into the chamber of housing 102. In an exemplary delivery system, plunger 108 and housing 102 are integral and should not be separated. Distal end 106 of housing 102 can be sealed with sealed cap 126 to prevent drying of the prepared tissue repair paste composition.

The user selects either the flexible tamping pair or the substantially rigid tamping pair for delivery and application of the prepared tissue repair paste composition to a tissue site. When the user is ready to deliver and apply the prepared tissue repair paste composition to the tissue site, cap 126 is removed and the tube (110 or 118) of the selected tamping pair is secured to distal end 106 of housing 102 by, for example, screwing the tube fitting (112 or 120) onto the housing distal end 106, thereby engaging spiral threads 132 on housing distal end 106 with spiral grooves in the fitting.

To deliver and apply prepared the tissue repair paste composition to the tissue site, the delivery system is positioned near the tissue site, and the distal end of the tube in contact with the tissue site. Plunger 108 is manually depressed, thereby expelling the tissue repair paste composition through housing distal end 102, through the tube (110 or 118), and out the distal end of the tube into the tissue site. When the chamber of housing 102 is empty, housing 102 can be detached from the tube. The tamping element of the selected tamping pair (i.e. if flexible tube 110 is being used, tamping element 114 is selected; if substantially rigid tube 118 is being used, tamping element 122 is selected). The tamping element is inserted into the tube to force any remaining tissue repair paste through the tube and into the tissue site. If at any time a tube clogs during use, housing 102 can be detached from the tube, excess tissue repair paste should be cleared from the proximal end of the tube, and the appropriate tamping element inserted into the tube to clear the clog. Housing 102, at least partially filled with the tissue repair paste composition, can be re-attached to the tube and application of the tissue repair paste composition can continue, as detailed above.

It will be understood that whichever tamping pair is first selected, can be switched out at any time during use for the other tamping pair. For example, if the flexible tamping pair is first selected, flexible tube 110 can be decoupled housing distal end 106, the proximal end of substantially rigid tube 118 can be coupled to housing distal end 106, and plunger 108 manually depressed thereby forcing the tissue repair paste through distal end 106 of the housing and into the lumen of substantially rigid tube 118. Further, housing 102 can be decoupled from substantially rigid tube 118, the distal end of substantially rigid tamping element 122 inserted into the lumen of substantially rigid tube 118 at the proximal end of substantially rigid tube 118, and substantially rigid tamping element 122 impelled through the lumen of substantially rigid tube 118, thereby forcing the tissue repair paste through the lumen of substantially rigid tube 118 to further deliver the tissue repair paste to the tissue site.

Alternatively, wherein the tamping pair selected in step (b) is the substantially rigid tamping pair, the method may further comprise: (g) decoupling the substantially rigid tube from the housing distal end; (h) coupling the proximal end of the flexible tube to the housing distal end; (i) depressing the plunger within the chamber thereby forcing the tissue repair paste through the distal end of the chamber and into the lumen of the flexible tube; decoupling the housing from the flexible tube; (j) inserting the distal end of the flexible tamping element into the lumen of the flexible tube at the proximal end of the flexible tube; and (k) impelling the flexible tamping element through the lumen of the flexible tube, thereby forcing the tissue repair paste through the lumen of the flexible tube to further deliver the tissue repair paste to the tissue site.

EXAMPLE

The following example is included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Example: Preparation of a Bone Graft Paste for Use in the Delivery System

When using autograft bone, use sterile gauze to remove as much liquid (i.e., blood or saline) as possible prior to mixing with InQu® Paste Mix PLUS powder. This will prevent over-hydration of the final mixed bone graft. When using autograft, the bone shavings should be cut to as small a size as possible (<2 mm in size). Optimal size bone shavings can be produced using high-speed burrs. If bone shavings remain 2 mm in size, clogging of the device cannula may occur. When preparing InQu® Paste Mix PLUS with autograft, the ratio of product to liquid should be approximately 5:3. Specifically:

For 10 cc of InQu Paste Mix PLUS, add 6 cc of liquid. For 5cc of InQu Paste Mix PLUS, add 3 cc of liquid. For 2.5 cc of InQu Paste Mix PLUS, add 1.5 cc of liquid. Proportions can be adjusted as desired for consistency. When preparing Preparation of InQu® Paste Mix PLUS without autograft the ratio of product to liquid should be approximately 5:4. Specifically:

For 10 cc of InQu Paste Mix PLUS, add 8 cc of liquid.
For 5cc of InQu Paste Mix PLUS, add 4 cc of liquid.
For 2.5 cc of InQu Paste Mix PLUS, add 2 cc of liquid.
Proportions can be adjusted as desired for consistency.

What is claimed is:

1. A delivery system for delivering a tissue repair paste composition to a tissue site in need of repair, the system comprising: an elongate housing defining a chamber for receiving the paste composition and having a proximal end and a distal end having an external surface; a plunger slidably disposed within the chamber; a flexible tube defining a lumen and comprising: a proximal end defining a fitting having an internal surface configured to reversibly engage with the external surface of the housing distal end; a distal end; and a peripheral wall; a malleable metal wire coupled to the peripheral wall of the flexible tube and extending at least the length of the tube from the proximal end to the distal end of the flexible tube, wherein the malleable metal wire provides flexibility, strength, and shape memory to the flexible tube; a flexible tamping element comprising a flexible rod configured to be slidably disposed within the lumen of the flexible tube; a substantially rigid tube defining a lumen and having a proximal end defining a fitting having an internal surface configured to reversibly engage with the external surface of the housing distal end; and a substantially rigid tamping element comprising a substantially rigid rod configured to be slidably disposed within the lumen of the substantially rigid tube.

2. The delivery system according to claim 1, further comprising a first cap having a peripheral wall defining a fastening element configured to reversibly engage the external surface of the chamber distal end, thereby sealing the distal end of the chamber.

3. The delivery system according to claim 2, wherein the cap further comprises a sealed female Luer Lok fitting.

4. The delivery system according to claim 1, wherein the flexible tamping element and the substantially rigid tamping element each have a proximal end defining a flange.

5. The delivery system according to claim 1, wherein the metal wire terminates at the distal end of the flexible tube and is capable of transmitting an imaging signal from the distal end of the flexible tube.

6. The delivery system according to claim 1, wherein the metal wire is capable of transmitting a fluoroscopy signal from the distal end of the flexible tube.

7. The delivery system of claim 1, wherein the flexible tamping element comprises a material having shape memory.

8. The delivery system of claim 1, wherein the flexible tamping element comprises polycarbonate.

9. The delivery system of claim 1, wherein the flexible tube comprises polyurethane.

10. The delivery system of claim 9, wherein the flexible tube further comprises silicone impregnated in the polyurethane.

11. The delivery system of claim 1, wherein the flexible tube comprises peripheral wall having an inner surface, the inner surface having a coating of a non-stick polymer.

12. The delivery system of claim 11, wherein the inner surface has a coating of a polytetrafluoroethylene (PTFE).

13. The delivery system of claim 1, wherein the tissue repair paste composition is a bone graft composition.

14. The delivery system of claim 1, wherein the chamber housing comprises a transparent plastic.

15. A method for delivering a tissue repair paste to a tissue site, the method comprising: (a) loading the tissue repair paste into the housing chamber of the delivery system according to claim 1; (b) selecting a tamping pair from a first tamping pair consisting of the flexible tube and the flexible tamping element, and a second tamping pair consisting of the substantially rigid tube and the substantially rigid tamping element; (c) coupling the proximal end of the selected tube to the distal end of the housing; (d) depressing the plunger within the chamber thereby forcing the tissue repair paste through the distal end of the chamber and into the lumen of the selected tube;
decoupling the housing from the selected tube; (e) inserting the distal end of the selected tamping element into the lumen of the selected tube at proximal end of the selected tube; and (f) impelling the tamping element through the lumen of the selected tube, thereby forcing the tissue repair paste through the lumen of the selected tube to deliver the tissue repair paste to the tissue site.

16. The method according to claim 15, wherein the tamping pair selected in step (b) is the flexible tamping pair, and the method further comprises: (g) decoupling the flexible tube from the housing distal end; (h) coupling the proximal end of the substantially rigid tube to the housing distal end; (i) depressing the plunger within the chamber thereby forcing the tissue repair paste through the distal end of the chamber and into the lumen of the substantially rigid tube; decoupling the housing from the substantially rigid tube; (j) inserting the distal end of the substantially rigid tamping element into the lumen of the substantially rigid tube at the proximal end of the substantially rigid tube; and (k) impelling the substantially rigid tamping element through the lumen of the substantially rigid tube, thereby forcing the tissue repair paste through the lumen of the substantially rigid tube to further deliver the tissue repair paste to the tissue site.

17. The method according to claim 16, wherein the tamping pair selected in step (b) is the flexible tamping pair, and the method further comprises flexing the flexible tube to form a bend in the tube, thereby to improve a surgical approach to the tissue site relative to a surgical approach obtained with a straight tamping pair.

18. The method according to claim 17, further comprising flexing the flexible tamping element to form a corresponding bend in the flexible tamping element.

19. The method according to claim 17, wherein the tissue site is a spinal site being approached using a TLIF (transforaminal interbody fusion) approach or using a PLIF (posterolateral interbody fusion) approach, the tissue repair paste comprises a bone graft paste composition, and the flexible tube is bent to deliver the bone graft paste composition to a contra-lateral space of the disc.

20. The method of claim 15, wherein the tissue site is a spinal site, and the tissue repair paste is a bone graft paste composition.

21. The method according to claim 15, wherein the tamping pair selected in step (b) is the substantially rigid tamping pair, and the method further comprises: (g) decoupling the substantially rigid tube from the housing distal end; (h) coupling the proximal end of the flexible tube to the housing distal end; (i) depressing the plunger within the chamber thereby forcing the tissue repair paste through the distal end of the chamber and into the lumen of the flexible tube; decoupling the housing from the flexible tube; (j) inserting the distal end of the flexible tamping element into the lumen of the flexible tube at the proximal end of the flexible tube; and (k) impelling the flexible tamping element through the lumen of the flexible tube, thereby forcing the tissue repair paste through the lumen of the flexible tube to further deliver the tissue repair paste to the tissue site.

22. The delivery system of claim 1, wherein the flexibility, strength, and shape memory provided by the malleable metal wire to the flexible tube is sufficient to allow bending and recovery of the initial straight shape of the flexible tube as needed during use.

23. A kit for delivering a tissue repair paste to a tissue site, the kit comprising: a tray comprising a sterilizable material; and disposed in the tray, a plurality of components of a delivery system for delivering the tissue repair paste to the tissue site, the components comprising: an elongate housing defining a chamber for receiving the paste composition and having a proximal end and a distal end having an external surface; a plunger slidably disposed within the chamber; a flexible tube defining a lumen and comprising: a proximal end defining a fitting having an internal surface configured to reversibly engage with the external surface of the housing distal end; a distal end; and a peripheral wall; a malleable metal wire coupled to the peripheral wall of the flexible tube and extending at least the length of the tube from the proximal end to the distal end of the flexible tube, wherein the malleable metal wire provides flexibility, strength, and shape memory to the flexible tube; a flexible tamping element comprising a flexible rod configured to be slidably disposed within the lumen of the flexible tube; a substantially rigid tube defining a lumen and having a proximal end defining a fitting having an internal surface configured to reversibly engage with the external surface of the housing distal end; and a substantially rigid tamping element comprising a substantially rigid rod configured to be slidably disposed within the lumen of the substantially rigid tube.

24. The kit according to claim 23, wherein the components of the delivery system further comprise a cap having a peripheral wall defining a fastening element configured to reversibly engage the external surface of the chamber distal end, thereby sealing the distal end of the chamber.

25. The kit according to claim 24, wherein the cap further comprises a sealed female Luer Lok fitting.

26. The kit according to claim 23, wherein metal wire terminates at the distal end of the flexible tube and is capable of transmitting an imaging signal from the distal end of the flexible tube.

27. The kit according to claim 23, further comprising an amount of the tissue repair paste in a separate container.

28. The kit according to claim 23, further comprising amounts of at least two reagents for preparing the tissue repair paste.

29. The kit according to claim 23, wherein the tissue repair paste composition comprises a bone graft composition.

30. The kit according to claim 23, further comprising a sealed cover.

31. The kit according to claim 23, further comprising a sealed pouch enclosing the tray and delivery system components disposed therein.

32. The kit of claim 23, wherein the flexibility, strength, and shape memory provided by the malleable metal wire to the flexible tube is sufficient to allow bending and recovery of the initial straight shape of the flexible tube as needed during use.

33. A delivery system for delivering a tissue repair paste composition to a tissue site in need of repair, the system comprising: an elongate housing defining a chamber for receiving the paste composition and having a proximal end and a distal end having an external surface; a plunger slidably disposed within the chamber; and a flexible tube defining a lumen and comprising: a proximal end defining a fitting having an internal surface configured to reversibly engage with the external surface of the housing distal end; a distal end; and a peripheral wall; a malleable metal wire coupled to the peripheral wall of the flexible tube and extending at least the length of the tube from the proximal end to the distal end of the flexible tube, wherein the malleable metal wire provides flexibility, strength, and shape memory; and a flexible tamping element comprising a flexible rod configured to be slidably disposed within the lumen of the flexible tube.

34. The delivery system of claim 33, wherein the flexibility, strength, and shape memory provided by the malleable metal wire to the flexible tube is sufficient to allow bending and recovery of the initial straight shape of the flexible tube as needed during use.

35. A kit for delivering a tissue repair paste to a tissue site, the kit comprising: a tray comprising a sterilizable material; and disposed in the tray, a plurality of components of a delivery system for delivering the tissue repair paste to the tissue site, the components comprising: an elongate housing defining a chamber for receiving the paste composition and having a proximal end and a distal end having an external surface; a plunger slidably disposed within the chamber; and a flexible tube defining a lumen and comprising: a proximal end defining a fitting having an internal surface configured to reversibly engage with the external surface of the housing distal end; a distal end; and a peripheral wall; a malleable metal wire coupled to the peripheral wall of the flexible tube and extending at least the length of the tube from the proximal end to the distal end of the flexible tube, wherein the malleable metal wire provides flexibility, strength, and shape memory to the flexible tube; and a flexible tamping element comprising a flexible rod configured to be slidably disposed within the lumen of the flexible tube.

36. The kit of claim 35, wherein the flexibility, strength, and shape memory provided by the malleable metal wire to the flexible tube is sufficient to allow bending and recovery of the initial straight shape of the flexible tube as needed during use.

* * * * *